United States Patent [19]
Casanova et al.

[11] Patent Number: 5,248,396
[45] Date of Patent: * Sep. 28, 1993

[54] PROCESS FOR PREPARING BUTANETETRACARBOXYLIC ACID

[75] Inventors: Eduardo A. Casanova, Ballwin; Dennis J. Kalota, Fenton; John H. Wagenknecht, Cedar Hill, all of Mo.

[73] Assignee: Monsanto Company, St. Louis, Mo.

[*] Notice: The portion of the term of this patent subsequent to Sep. 14, 2010 has been disclaimed.

[21] Appl. No.: 450,767

[22] Filed: Dec. 14, 1989

[51] Int. Cl.⁵ ............................................. C25B 3/00
[52] U.S. Cl. ................................................ 204/59 R
[58] Field of Search ................................... 204/59 R

[56] References Cited

U.S. PATENT DOCUMENTS

| | | | |
|---|---|---|---|
| 3,274,084 | 9/1966 | Baizer | 204/72 |
| 3,390,066 | 6/1968 | Baizer | 204/72 |
| 4,076,601 | 2/1978 | White | 204/59 R |
| 4,659,441 | 4/1987 | Noding | 204/59 R |

OTHER PUBLICATIONS

Morrison et al "Organic Chemistry" 3rd ed. Allyn and Bacon Inc., Boston, 1973, pp. 680–681.
Baizer et al "Organic Electrochemistry An Introduction and Guide" 2nd ed, Marcel Dekker, Inc. New York, 1983, p. 200.
CA 74:75980f p. 407 (Giovanni et al).
CA 90:5921u p. 543 (Tari et al).
CA 96:34508u p. 602 (White).

*Primary Examiner*—John Niebling
*Assistant Examiner*—Kishor Mayekar
*Attorney, Agent, or Firm*—W. W. Brooks

[57] ABSTRACT

1,2,3,4-Butanetetracarboxylic acid is prepared by electrohydrodimerization of dialkyl maleates in alkanol to produce tetraalkyl butanetetracarboxylates, followed by hydrolysis of the resultant tetraalkyl butanetetracarboxylates to obtain the butanetetracarboxylic acid product.

13 Claims, 6 Drawing Sheets

PROCESS FOR PREPARING BUTANETETRACARBOXYLIC ACID

BACKGROUND OF THE INVENTION

1. Field of the Invention

The present invention is directed to a process for preparing 1,2,3,4-butanetetracarboxylic acid by electrohydrodimerization of dialkyl maleates in alkanol to obtain tetraalkyl butanetetracarboxylates, followed by hydrolysis to obtain butanetetracarboxylic acid; and including oxidative purification for removing color-causing impurities from the butanetetracarboxylic acid.

The compound 1,2,3,4-butanetetracarboxylic acid has been found by the U.S. Department of Agriculture to be an effective permanent press agent for polyester-cotton blend fabrics, and the compound could find use in large quantities for such purpose. Accordingly, an efficient process for preparing the compound could be very useful. Such a process must produce a product of acceptable color performance properties, as this is an important factor for suitability for permanent press agents.

2. Description of the Related Art

Procedures have been reported in which 1,2,3,4-butanetetracarboxylic acid is prepared by oxidative cleavage of tetraphthalic acid or anhydride by oxidation with ozone-containing gas, followed by molecular oxygen-containing gas, with the mixture then being heated with a peroxide, e.g. $H_2O_2$, at 100° C. to produce the butanetetracarboxylic acid; see Japanese patent 55/49336 [80/493363], Apr. 9, 1980, Chem. Abstracts 93 (13) 132082h; and Japanese patent 54/151906 [79/151906], Nov. 29, 1979, Chem. Abstracts. 92(23) 197937g. Also reported is a procedure in which Delta-4-tetrahydrophthalic anhydride was oxidized with $HNO_3$, then stirred one hour at 90° C. (oxidative post treatment) to give 1,2,3,4-butanetetracarboxylic acid free of $HNO_3$, which gave no color on heating 30 minutes at 140° C. in ethylene glycol. Polycarboxylic acids from the $HNO_3$ oxidation of $C_{5-16}$ cycloalkenes were purified by an oxidative post treatment; see German Offen. DE 3016225 Al, Oct. 29, 1981, Chem. Abstracts, 96(3), 19672z.

The present invention involves a different route to butanetetracarboxylic acid, involving hydrolysis of tetraalkyl butanetetracarboxylates, which are obtained by electrolytic hydrodimerization of dialkyl maleates in alkanols Electrolytic reductive couplings of various activated olefins have been investigated and reported in the past. Much of this work involved aqueous systems in a divided cell, and often with a supporting electrolyte salt with a very negative discharge potential, such as a quaternary ammonium salt. In addition to reductive couplings, other reactions such as simple reduction and polymerization frequently occur. Various parameters of such reactions have been discussed, including use of various electrolytes, see Organic Electrochemistry, edited by Manuel M. Baizer and Henning Lund (1983, Marcel Dekker, N.Y., N.Y.). At page 669 of this reference, it is stated that undivided cells are operable with the restrictions that (1) the olefin and product not be substantially oxidized at the anode, and (2) the oxygen evolved at the anode in aqueous systems not promote undesirable side reactions. This reference also refers, e.g. at pages 669 and 672, to dimerization of diethyl maleate and the effect of alkali metal cations in increasing the rate of dimerization of anion radicals.

Electrolytic hyrodimerization of diethyl maleate has been reported by Baizer and Petrovich, J. Electrochem. Soc., 114(10), 1024–1025 (1967); the described procedures utilized a catholyte of water and dimethylformamide in a divided cell and indicated, all other conditions being the same, more hydrodimerization occurs in the presence of tetraethylammonium ion than of sodium ion. The electrolyses were carried out for three (3) hours, generally resulting in about 50% conversions, and specified amounts of hydrodimer, and other products.

Methanol has been used as a solvent for study of reduction mechanisms. See Dimitra Sazou et al, "Electrochemical Reduction of Maleic and Fumaric Acids and Their Dimethyl Esters in Methanol at a Mercury Electrode", Coll. Czech. Chem. Comm., 52, 2132–2141 (1957). Cyclic voltammograms of the acids in methanol solution with various supporting electrolytes, employing a hanging mercury drop electrode, are given, and reduction mechanisms discussed. The double bond reduction of the corresponding dimethyl esters was stated to take place in one step. The described procedures utilized very dilute solutions of the acids, e.g. 0.0025 or 0.005 moles per liter.

SUMMARY OF THE INVENTION

The invention involves an efficient procedure capable of converting dialkyl maleates to tetraalkyl butanetetracarboxylates in high yields and conversions by electrolytic hydrodimerization in alkanols, coupled with an efficient process for hydrolyzing the tetraalkyl butanetetracarboxylates to butanetetracarboxylic acid. The electrolytic hydrodimerization provides the tetraalkyl butanetetracarboxylates in alkanol solution, a form suitable for isolution-purification by crystallization, which contributes to the purity of the butanetetracarboxylic acid produced therefrom. Some aspects of the invention relate to the acid preparation reaction, while others concern the electrolysis reaction.

The present invention involves a process for preparing 1,2,3,4-butanetetracarboxylic acid (BTCA) of high purity and very low or negligible levels of color-causing materials, from tetraalkyl butanetetracarboxylates (TABTC) utilizing efficient reactions, conditions and procedures which give good yields and recoveries of product having good purity and acceptable performance in color tests. In a particular aspect, the invention involves hydrolyzing a tetraalkyl butanetetracarboxylate to the butanetetracarboxylic acid utilizing relatively high TABTC and acid catalyst contents, compared to water, so as to give a good reaction rate and desirably short reaction time, such as within six hours; and distilling over alkanol and water during the hydrolysis to drive the reaction while adding additional water to replace that distilled.

The invention also involves crystallizing the tetraalkyl butanetetracarboxylate from alkanol before the hydrolysis step in order to separate certain by-products from the tetracarboxylate, and particularly in the case of tetramethyl butanetetracarboxylate (TMBTC), crystallizing from methanol at sub-zero (Celsius) temperatures, e.g. near −10° C., and also optionally adding water to aid in the separation and high recovery.

The invention further involves subjecting the butanetetracarboxylic acid to treatment with an oxidizing agent to effect oxidation of color-causing materials, with an oxidation with aqueous hydrogen peroxide at elevated temperatures up to 55° C., followed by higher temperatures to destroy excess peroxide, being very effective.

The invention can also advantageously use, prior to the hydrolysis step, an aqueous washing procedure in which the tetraalkyl butanetetracarboxylate, at temperature above its melting point, is extracted with an aqueous liquid, e.g. water, in order to remove salts and other water soluble impurities, including some color-causing materials.

The invention can also employ a crystallization procedure as a convenient and efficient means to separate the butanetetracarboxylic acid product from aqueous solution, with cooling to ambient temperatures generally being sufficient to effect crystallization. The fraction of butanetetracarboxylic acid which does not separate can be recycled with filtrate, containing residual acid catalyst, to the hydrolysis step.

The present invention provides a process for preparing butanetetracarboxylate from tetraalkylbutanetetracarboxylates with high yield and recovery, e.g. about 83%, by a series of relatively simple reactions and operations which can be accomplished with industrially practical equipment and with reason-able production rates.

The present invention also involves a useful preparative process for tetraalkylbutane tetracarboxylates which comprises effecting electrolytic hydrodimerization of substantial concentrations of dialkyl maleate in a medium comprising alkanol, with marked advantage in the selectivities and yields obtained, and conditions which can be employed. The invention further involves effecting such hydrodimerization in an undivided cell employing a metal salt, particularly an alkali metal salt, as supporting electrolyte. The alkanol, employed in substantially dry form, can serve as a proton donor to effect addition of hydrogen ion during the reaction. The use of alkanol, rather than water as the electrolysis medium, substantially avoids hydrolysis of the maleate ester groups, and the acidification of the medium which would result from such hydrolysis. It has been found, surprisingly, that in an alkanol medium, with an undivided cell, good yields of tetraalkylbutanetetracarboxylate can be obtained, and that the yields in electrolyses employing sodium or other alkali metal salts can even exceed those in electrolyses employing tetraalkylammonium salts. The presence of alkanol essentially prevents hydrolysis of the dialkyl maleate, even in the presence of basic salts, as solvolysis of an alkyl group replaces it with an alkyl group. Therefore alkyl acid maleate is not formed in significant quantity, and the medium does not become strongly acidic. The hydrodimerization can therefore be carried to high conversion with good yields of hydrodimer, rather than with increasing amounts of reduction product, dialkyl succinate, resulting from acidification of the medium, as characteristic of electrolytic hydrodimerizations of dialkyl maleate in aqueous media. In aqueous media there is a shift from alkaline to acidic conditions during the electrolysis, and pH usually declines to about 4. In the absence of water in an alkanol medium, such acidic pH conditions do not develop and a marked increase in succinate product is not observed. The present process is marked by an absence of substantial amounts of monoalkyl maleate in the electrolysis medium. It is very advantageous that the present process can be conducted efficiently in an undivided cell, thereby avoiding the additional electrical resistance, membrane expense, and other adverse factors involved in operating with a divided cell. The invention generally involves use of electrolysis solution with very substantial concentrations of maleate reactant and use of fairly substantial electrical current in the electrolysis, and obtaining substantial amounts of tetraalkyl butanetetracarboxylate product in reasonable reaction time.

DESCRIPTION OF THE REFERRED EMBODIMENTS

Figure 1:
FIG. 1 is a drawing with bar graphs illustrating yields of tetramethyl butanetetracarboxylate and other products obtained by electrolysis in methanol with various electrolytes.

In accordance with the present invention, a process is provided for the preparation of 1,2,3,4-butanetetracarboxylic acid. The process involves converting dialkyl maleates to tetraalkyl butanetetracarboxylates in high yields and conversions by electrolytic hydrodimerization in alkanols, and hydrolyzing the resultant tetraalkyl butanetetracarboxylates in acidic media to obtain butanetetracarboxylic acid. Purification of the resultant butanetetracarboxylic acid provides a product having sufficient purity and freedom from objectionable levels of color-causing contaminants to be suitable for use as an effective permanent press agent for polyester-cotton blend fabrics.

Electrolytic Hydrodimerization

The electrolytic hydrodimerization step of present process can be conducted with dialkyl maleates in general, but for practical considerations, only the maleates with lower alkyl groups, e.g. of 1 to 6 carbon atoms, are likely to be of much interest. Dimethyl maleate (DMM) is the preferred reactant, and is used in exemplifications herein, but diethyl maleate, dipropyl maleate, dihexyl maleate, etc. can be used. Electrical resistance tends to increase with increasing alkyl size, whether in the ester or in the alkanol solvent, thereby making electrical power usage less efficient. It is also disadvantageous to employ alkanols of such high molecular weight that they tend to be solids at ambient temperature. The tetraalkyl butaneteracarboxylates are used for conversion to butanetetracarboxylic acid as described herein. The simplest ester, the tetramethyl ester, serves very well for this purpose and there will ordinarily be no reason to choose other tetraalkyl esters as intermediates for the same product.

The reactions presumably occurring in the electrolysis of the present process can be pictured:

cathode:

-continued

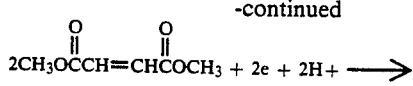

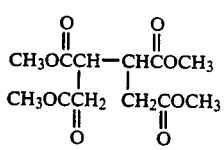

anode:

$$2CH_3OH - 2e \longrightarrow 2H+ + CH_3OCH_2OH$$

Sum:

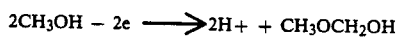

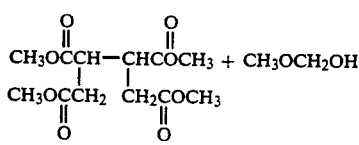

Methoxymethanol, the hemiacetal of formaldehyde, is also a likely product. The presence of formaldehyde has been confirmed, however, its presence may be due to disassociation of methoxymethanol. Additional possible intermediates include $+CH_2OH$ and $\bullet CH_2OH$ in the anode reaction, and acetic acid from protons and acetate electrolyte (if used). Also, alkoxides, e.g. $CH_3O^-$, can be produced as a result of reaction at the cathode.

With $\bullet CH_2OH$ as a likely intermediate at the anode, it presents the possibility of adding at the maleate double bond to cause production of other by-product, thereby possibly causing considerable loss in selectivity to the desired hydrodimer when an undivided cell is used; however, this undesirable side reaction does not appear to occur to any significant extent as good results are obtained in an undivided cell. It may be that the use of an undivided cell is actually advantageous, as it permits protons generated at the anode to move very freely to protonate methoxide produced in conjunction with the hydrodimerization at the cathode, thereby avoiding possible interfering reactions of the methoxide and polymerization.

It has fortunately been found that the present electrolysis can not only be carried out very efficiently with simple alkali metal salts as supporting electrolyte, but that the results with such salts are actually better than those obtained with some of the more expensive electrolytes which are commonly used. In addition to the preferred alkali metal salts, the present process can use other supporting electrolytes known to the art.

The electrolysis uses supporting electrolytes to provide ions to carry the current in the process. In general, any electrolytes can be employed which dissociate into ions in the electrolysis medium to carry current, and which do not unduly interfere with the desired reactions or cause excessive losses to competing reactions. Most of the electrolytes can be considered salts, as having a cation from a base and an anion from an acid. However, it is also feasible to employ bases as the electrolytes, and this may at times be appropriate in order to counter acidity. The dialkyl maleates are subject to reduction at less negative potentials than many suitable cations, so competitive discharge of cations is not ordinarily a concern. Alkali metal compounds such as sodium, potassium or lithium compounds, can be employed, as well as alkaline earth metal compounds, and quaternary ammonium compounds, which are characterized by very negative discharge potentials. Acid anions will in general be operative as the anionic portion of the electrolyte, but will generally be selected to have acceptable solubility in the alkanol system, and to minimize interfering or competing reactions and electrode degradation. Among operable anions are carboxylic acid anions, halide ions, and aromatic sulfonic acid anions.

In the present invention it has fortunately been found that a very simple salt, e.g. sodium acetate, serves very well as an electrolyte in the electrohydrodimerization of alkyl maleates. In the prior art quaternary ammonium salts have usually been considered to give better results in electrohydrodimerization than do alkali metal salts. However, in the present invention alkali metal salts have been found capable of giving better results in the electrohydrodimerization of dimethyl maleate, particularly with respect to selectivity to desired product. Among the useful electrolytes are sodium, potassium and lithium acetates, propionates, and succinates, sodium toluenesulfonates, tetrabutylammonium p-toluenesulfonate, tetrabutylammonium hydroxide, tetrabutylammonium acetate, tetrabutylammonium chloride. Similar salts can be used with sulfate, phosphate and tetrafluoroborate anions, but such salts tend to cause anode degradation when preferred graphite anodes are used. Some halide salts, e.g. sodium halide, have very limited solubility in methanol, and are therefore inconvenient for use. With regard to calcium chloride, the chloride is theorized to be relatively tightly bound to the calcium and to act as an acid catalyst to cause formation of dialkyl 2-methoxysuccinate (conveniently referred to herein as methoxydialkylsuccinate), making selectivity very poor to the desired hydrodimer. Calcium acetate has poor solubility, but calcium nitrate is better in this regard.

The present electrolysis process can be carried out over a broad range of electrolytic conditions, including a wide range of strengths of applied electric currents and current densities at the electrodes. The process is operable at very low current densities, such as less than 5 milliamperes per square centimeter to more than 100 or 200 milliamperes per square centimeter. Preferred current densities are apt to be in the range of about 15 to about 50 or so milliamperes per square centimeter, with operation, for example at 25 milliamperes per square centimeter giving good product selectivity at relatively low cell voltage, with good electrode life. There is advantage in having high current density in order to maximize cell utilization, but this is to be balanced against the high cell voltage and resistance and heat generation which add to costs.

The present electrolysis can be operated over a broad range of concentrations, such as from less than about 5% to more than about 50% by weight of the dialkyl maleate reactant, and good selectivities to the desired dimer products are obtainable over broad ranges. Concentrations from at least 15% to 35% to 40% or so are usually very suitable, and product concentrations in the same range are also very suitable, although they will be lower in specific cases because of less than 100% yields and conversions. The process is suitable for large scale production, making kilogram or more quantities of product. The use of relatively high concentrations of reactant lessens the amount of materials to be handled.

However, the electrical resistance of the solution rises with the concentration of reactant. In addition, solubility considerations may be a factor at some higher concentrations. It is desirable, although not necessary, to operate with all components in a homogeneous phase during the electrolysis.

The concentration of supporting electrolyte can vary widely, but it is unnecessary to have more than very dilute concentrations for conductivity. Higher concentrations will improve conductivity, but salts in general are not very soluble in methanol, and there is ordinarily no advantage in using amounts of salts in excess of their solubility. The amount of salt can be just a minimum amount to give electrical conductivity, but will generally be in a range of 0.5 to 2 or 3% or so by weight, and for practical purposes, seldom over 5% or so by weight. In order to minimize expense, the salt concentrations will be kept low, as the cost of replenishing or recycling the salts will increase with the amount of the salt. The preferred operation will employ a relatively inexpensive salt, e.g. sodium acetate, which can be disposed of, rather than recycled.

The concentration ranges of maleate reactant set forth herein are, in general, initial concentrations, as the concentration will change during the electrolysis process, which will generally be run as a batch reaction, or a series of batch reactions. The electrolysis reaction will ordinarily be run to fairly high conversion, reacting more than 75% or 80% of the maleate, because selectivity to desired product is still good at high conversions, and in order to avoid unnecessary steps, handling and expense in separating unreacted maleate from the dimer product for recycle. It will be preferred to operate at maleate conversions approximately 95% or so. Higher conversions are possible, but it has been found that significant electrode degradation occurs if the electrolysis is continued with little or no maleate reactant present.

It has been found that there is a competing chemical side reaction which produces methoxydimethylsuccinate. The amount of this reaction is generally dependent upon the time of exposure of the maleate reactant to the components of the reaction system. Therefore it may be desirable to operate the electrolysis as a series of batch reactions, with relatively low initial maleate concentration and addition of more maleate in subsequent batches of the series. The last batch could then be taken to high conversion prior to product separation. Another approach to minimizing maleate contact time is to use an electrolysis cell which is large, particularly with respect to electrode surface area, compared to the amount of material in the reaction system and maleate reactant. Another approach is a constant stirred tank reactor with a continuous feed and discharge where the DMM concentration is maintained low to diminish the chemical driving force for this side reaction.

The control of electrolytic reaction time can also be expressed in terms of electrical current supply. The conversion of a particular amount of maleate reactant requires a corresponding number of ampere-hours of current, and the time to accumulate a requisite number of ampere-hours in an electrolysis can be varied by changing the current, or the number, or size of electrolysis cells. A reaction in accord with descriptions herein within 15 hours is fairly efficient, but a reaction time of no more than 10 hours will give less by-product. If the same current is involved, a 16-cell aggregate as described herein will accumulate ampere hours at twice the rate of an 8-cell aggregate. Of course, the 16 cells also use higher voltage for equivalent current. Cells for large scale production are contemplated as using at least 5 amperes, and more likely 10 or more amperes. Taking into consideration the amperage and number of cells employed, the present process will ordinarily use current and maleate amounts such that no more than 100 grams of dimethyl maleate are present per cell-ampere, and preferably less than 50 grams, or possibly even less than 25 grams dimethyl meleate per cell-ampere. (The term cell-ampere is number of cells x amperes, and is equivalent to ampere-hours per hour).

The present electrolysis can be effected with the usual electrodes employed in electrohydrodimerization and other reductive coupling reactions. Various metal and graphite electrodes are suitable. The preferred electrodes will generally have relatively high hydrogen overvoltages, such as greater than that of copper. However, lower overvoltage electrodes can be used. Among the cathode materials which can be used are graphite, graphite felt, mercury, copper amalgam, gold, copper, cadmium, tin and aluminum, with graphite, graphite felt, and lead being among the better materials. Mercury is an effective cathode, but its liquid state makes it unsuitable for common flow cell Configuration. Graphite electrodes, whether plate or felt, have been found to give the best results. It is an advantage of the present process, and surprising, that it can be conducted with superior results at graphite electrodes. Graphite is much less expensive than many other electrode materials, such as platinum or even lead or cadmium electrodes, does not add heavy metals to the solution via corrosion and is suitable for anodes as well as cathodes.

The present electrolysis can be carried out well with an alkanol, e.g. methanol, as the only material employed as carrier for the maleate ester and electrolyte salt. Ordinary industrial grades of methanol, which are substantially water-free, are very suitable for use. Traces of water picked up from contact with the atmosphere will not ordinarily be sufficient to affect results. For example, 2000 ppm water in solution has negligible effect. However, presence of more than traces of water will preferably be avoided, as even a small percentage of water can cause a decline in selectivity, and presence of more than, say 5% by weight, of water is very undesirable. If desired, co-solvents can be used along with the alkanol, particularly such aprotic solvents as dimethyl formamide and dimethyl sulfoxide or acetonitrile. Use of co-solvents will not generally be desirable, but there may be particular cases where solubility or other factors would make co-solvents worthwhile.

At the end of the electrolysis reaction the tetraalkyl butanetetracarboxylate product is present in solution in the electrolysis medium, for example, at a concentration of about 25% by weight. The tetraalkyl butanetetracarboxylate product can be separated by crystallization from the solution, followed by filtration. In the case of tetramethyl butanetetracarboxylate (TMBTC), the crystallization is effected by cooling, e.g. to below 0° C., usually between 0° C. and −10° C. The separation removes the product from the electrolysis medium and also separates it from residual maleate reactant and succinate and alkoxysuccinate by-products. The butanetetracarboxylate tetraester product can then be subjected to hydrolysis and purification procedures to prepare butanetetracarboxylic acid suitable for permanent press use.

Hydrolysis of Tetraalkyl Butanetetracarboxylates

The hydrolysis step of the present process for converting tetraalkylbutanetetracarboxylates to butanetetracarboxylic acid involves a hydrolysis to form the acid, and also various isolation and purification procedures in order to obtain product of acceptable purity and lack of objectionable levels of color-causing contaminants.

The exemplary process includes the following steps:
1. Filtration of TMBTC methanol solution to remove particulates;
2. Crystallization of TMBTC from solution and separation by filtration or centribugation;
3. Extraction of TMBTC with water to remove salts;
4. Hydrolysis of TMBTC to produce BTCA;
5. Oxidation of BTCA solution to remove color-forming impurities;
6. Crystallization of the BTCA from aqueous solution and separation by filtration or centrifugation; and
7. Washing the crystalline BTCA with water to remove residual acid; or
7A. Removing residual acid by partial or complete neutralization with base such as sodium hydroxide, and separating the crystalline BTCA by filteration or centrifugation.

At times there may be a preference to provide the BTCA in aqueous solution for use, rather than separating and washing it as in steps 6 and 7 above. While removal of residual acid is important for comparison purposes as the acid has a significant effect upon color development, in some applications the effect can be countered by and left to subsequent treatments. In the exemplary process, tetramethyl butanetetracarboxylate is used as exemplary of tetraalkyl butanetetracarboxylates which can be employed in the process under similar conditions, generally employing the corresponding alkanol as solvent. Since TMBTC serves very well as an intermediate to prepare the desired BTCA there will ordinarily be no need to use other tetraalkyl butanetetracarboxylate esters to prepare BTCA. However, tetraethyl butanetetracarboxylate and ethyl alcohol can be used under similar conditions with similar results.

The hydrolysis reaction involved in the present invention is represented:

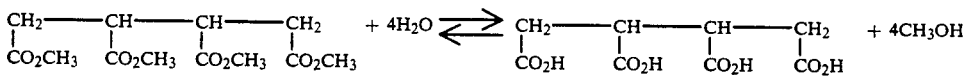

The reaction involves reaction of water with the tetramethyl ester, and in such reactions the amount of reaction, or equilibrium concentrations of the reaction, depends upon the concentration of the reactants, including the water. The reaction can be driven to the right, improving the conversion of the tetramethyl butanetetracarboxylate, by increasing the water concentration. Often hydrolysis reactions employ a very large amount of water, with the ester to be hydrolyzed constituting, for example, only about 10% by weight of the hydrolysis solution. Also such reactions are typically effected with fairly dilute acid catalyst concentrations, e.g. about 1 to 5% acid by weight. With tetramethyl butanetetracarboxylate, it has been found that low ester and low acid concentrations give very poor reaction rates. Such low rates would necessitate batch reaction time of 20 to 24 hours or so. In the present invention it has been found that high concentrations of TMBTC and acid catalyst give good reaction rates and permit relatively short batch reaction times, such as 4 to 5 hours or so. In such reactions, the BCTA is present in weight concentrations upwards of 20%, such as in a range of about 25 to 35% or more of the hydrolysis reaction mixture. The acid, such as sulfuric acid, is employed in amounts constituting more than 5% by weight of the reaction mixture and more than 10% by weight of the water present in the hydrolysis mixture. Considering the total hydrolysis mixture, it is advantageous to have at least one gram-equivalent acid per kg of hydrolysis mixture. In order to have good acid strength, it is advantageous to limit the amount of water present. However, water is a reactant for the hydrolysis and is needed for this purpose.

In an exemplary procedure herein, a desired limited amount of water is added initially, and as water is used in the reaction, or removed by distillation, additional amounts of water are added to maintain approximately the original water content. During the hydrolysis, methanol is removed by distillation in order to drive the reaction by removing a product; and water is distilled along with the methanol. It happens that a relatively large amount of water is employed during the course of the hydrolysis with, for example, a total of 1454 parts water being added and 1438 parts being removed by distillation in an operation in which about 260 parts water was present initially. The present invention includes a procedure in which water content in the hydrolysis mixture is relatively limited, such as near 50% or so or in the range of about 50% to about 75%, and large additional amounts of water are added to replace water as it is removed during the hydrolysis, such as more than 3 or 4 times the initial water provided. The controlled water content is used in conjunction with relatively high acid concentrations, such as more than 10% by weight of the water present. In regard to the total reaction mixture, it is desirable to have at least 0.6 gram-equivalent acid per kg of reaction mixture, and advantageously, more than about 1 gram equivalent acid, and more than 1.5 gram-equivalents acid has further advantage.

The invention is illustrated by the following examples. Further exemplification of the present invention is provided by several hydrolysis procedures involving hydrolysis of tetramethyl butanetetracarboxylate as described in Examples 8 through 13 below, with the procedures being summarized in Table 5. Data from Examples 10 through 13 have also been used for graphs illustrating the effects of temperature and concentration upon hydrolysis rate, as presented in FIGS. 3 through 5, and further described below.

ELECTROLYTIC HYDRODIMERIZATION

Example 1

An electrolysis was carried out in a jacketed resin pot, using water as an electrolysis medium, with dimethyl maleate present as a second phase, constituting 22% by weight of the electrolysis medium. The cathode was lead, and the anode was platinum. A mixture of tetrabutylammonium nitrate and tetrabutylammonium hydroxide was employed as electrolyte, and electrolysis was conducted at a current density of 30 milliamperes per square centimeter of cathode surface. The electrolysis began at a basic pH, but rapidly became more acidic due to base catalyzed hydrolysis of dimethyl maleate, leading to monomethyl maleate. The pH quickly approached a value of 4. Analysis showed a weight ratio of 47 parts tetramethyl butanetetracarboxylate to 22 parts of dimethyl succinate, a simple reduction product of the starting maleate. This amounts to a selectivity of only 2.1 parts hydrodimer to 1 part of the succinate material. It is apparent that the acidic conditions are causing a large loss to a simple reduction reaction, and that even the use of a basic electrolyte did not prevent the development of acidic conditions. The analysis of the electrolysis medium also showed unreacted dimethyl maleate, with it being present in a ratio of 41 parts to the 47 and 22 parts of hydrodimer and succinate products. Thus the reaction had been taken to only a relatively low conversion. Similar results were obtained in other runs with aqueous media, employing the undivided resin pot cell and graphite or lead cathodes with platinum anodes, at current densities varying from 30 to 70 milliamperes per square centimeter. Electrolytes utilized included tetrabutylammonium nitrate, tetraethylammonium p-toluenesulfonate, tetrabutylammonium hydroxide and tetrabutylammonium sulfate. The ratio of hydrodimer to succinate varied from the 2.1 reported above, to 0.43, with higher values being obtained when excess tetrabutylammonium hydroxide was present in an attempt to maintain a high pH.

Example 2

Electrolyses were carried out utilizing an undivided resin pot cell as described in Example 1, but using methanol as the medium. Results for a number of electrolyses, with quaternary ammonium electrolytes with some variation in conditions and electrodes, are set forth in Table 1. In the Table, the numerical values for dimethyl maleate (DMM) dimethyl succinate (DMS), and tetramethyl butanetetracarboxylate (TMBTC) are reported in terms of analytical values, which an be compared to give the ratios of the reported materials. The ratio of TMBTC to DMS ranged from as high as 2.55 in Run 1, down to 0.89 in Run 3, with the results in general being better than those with water as solvent. The Runs 5 and 6 used, respectively, 90% methanol and 33% methanol, with the results being inferior to those obtainable with undiluted methanol.

TABLE 1

| Run | Elec | Cath | Anode | Pl | Temp | CD | DMM | DMS | MeODMS | TMBTC |
|---|---|---|---|---|---|---|---|---|---|---|
| 1 | TBAFB | Gr | Pt | 26 | 25 | 70 | 68 | 29 | | 74 |
| 2 | TBAFB | Hg | Pt | 26 | | 40 | 5 | 18 | 35 | 45 |
| 3 | TBAFB | Gr | Pt | 26 | | 70 | 9 | 45 | | 40 |
| 4 | TBAH | Gr | Gr | 26 | | 70 | 0 | 39 | | 42 |
| 5 x | TBAFB | Gr | Pt | 25 | | 70 | 20 | 30 | | 55 |
| 6 xx | TEAT | Pb | Pt | 15 | | 30 | 31 | 35 | | 41 | x 90% methanol in water
xx 33% methanol in water

In Table 1 and elsewhere in the specification abbreviations will at times be used as designations as follows:
DMM is dimethyl maleate;
DMS is dimethyl succinate;
MeODMS is methoxydimethyl succinate;
TMBTC is tetramethylbutane tetracarboxylate;
TBAFB is tetrabutylammonium tetrafluoroborate;
TBAH is tetrabutylammonium hydroxide;
TEAT is tetraethylammonium-p-toluenesulfonate;
Pl is the payload in % by weight DMM in solution; and
CD is current density in milliamperes/cm$^2$

Example 3

The undivided resin pot cell of Example 1 was utilized with methanol as the medium and small concentrations of metal salts as electrolyte, with results reported in Table 2.

TABLE 2

| Run | Elec | Cath | Anode | Pl (%) | Temp (°C.) | CD (mA/cm$^2$) | DMM | DMS | MeODMS | TMBTC |
|---|---|---|---|---|---|---|---|---|---|---|
| 1 | NaOAc | Felt | Gr | 25 | 15 | 50 | 0 | 12 | 2 | 86 |
| 2 | Na$_2$Suc | Gr | Gr | 25 | 15 | 50 | 0 | 22 | 32 | 55 |
| 3 | KOAc | Gr | Gr | 26 | 27 | 70 | 1.7 | 8.2 | 1.8 | 15.6 |
| 4 | LiOAc | Gr | Gr | 26 | 28 | 70 | 2.5 | 4.5 | 1.5 | 16.2 |

It is demonstrated that good selectivities can be obtained by employing alkali metal salts in methanol, as seen from the 7.17 hydrodimer to succinate ratio (86/12) in Run 1, with sodium acetate and high conversions were also obtained as shown by the low or zero values for dimethyl maleate in the product solution.

Example 4

Electrolyses were conducted in a small flow cell of parallel plate design with a gap between electrodes of about 1 mm, and cathodes of 19 cm$_2$. Flow through the cell was at about 1 liter/minute. The cell was connected to a jacketed reservoir which was cooled by tap water (at about 15° C.). Electrolyses were conducted with dimethyl maleate, and about 1% by weight of a selected metal salt, in methanol, with results as reported in Table 3.

TABLE 3

| Run | Elec | Cath | Anode | Pl (%) | Temp (°C.) | CD (mA/cm$^2$) | DMM | DMS | MeODMS | TMBTC |
|---|---|---|---|---|---|---|---|---|---|---|
| 1 | NaOAc | Gr | Gr | 44 | 25 | 50 | 15 | 20 | 6 | 71 |
| 2 | LiOAc | Gr | Gr | 42 | 27 | 50 | 47 | 13 | 7 | 37 |
| 3 | LiOAc | Gr | Gr | 26 | 27 | 50 | 9 | 34 | 3 | 59 |

While there was considerable variation in these and other results in the cell, ratios of dimer to succinate as high as 3.5 were obtainable employing alkali metal salts in methanol.

Example 5

Electrolyses of dimethyl maleate were carried out in methanol employing various electrolytes. The electrolysis cell was a jacketed resin pot of 150 ml capacity, fitted with a magnetic stirring bar, graphite plate electrodes (5 cm by 5 cm by 0.5 cm) with 25 $cm_2$. of cathode surface facing the anode. The cell was cooled with tap water (15 to 20° C.) Power was supplied by a constant current power supply, generally set at 1 ampere. The cell was charged with 75 g methanol, 25 g dimethyl maleate, and 1 to 2 g of supporting electrolyte. Electrolysis was started and continued until nearly all of the dimethyl maleate was consumed as determined by gas chromatography. Selectivity to the three major products (as a percentage of the three products) was determined by gas chromatography, and shown in the bar graphs of FIG. 1. It will be noted that high TMBTC selectivities are obtained with the alkali metal acetates, particularly with lithium and sodium acetates. The illustrated results are based on generally comparable procedures. While other results may be obtained under other conditions, the illustrated results show that high selectivities are obtainable, and this is consistent with the selectivities consistently obtainable, particularly with sodium acetate, under standard conditions in other procedures. Halide anions were operable, although at a very low selectivity with $CaCl_2$. The high levels of methoxydimethylsuccinate indicate that use of $CaCl_2$ and LiCl results in catalytic methoxylation, a competing reaction.

Example 6

Figure 2:
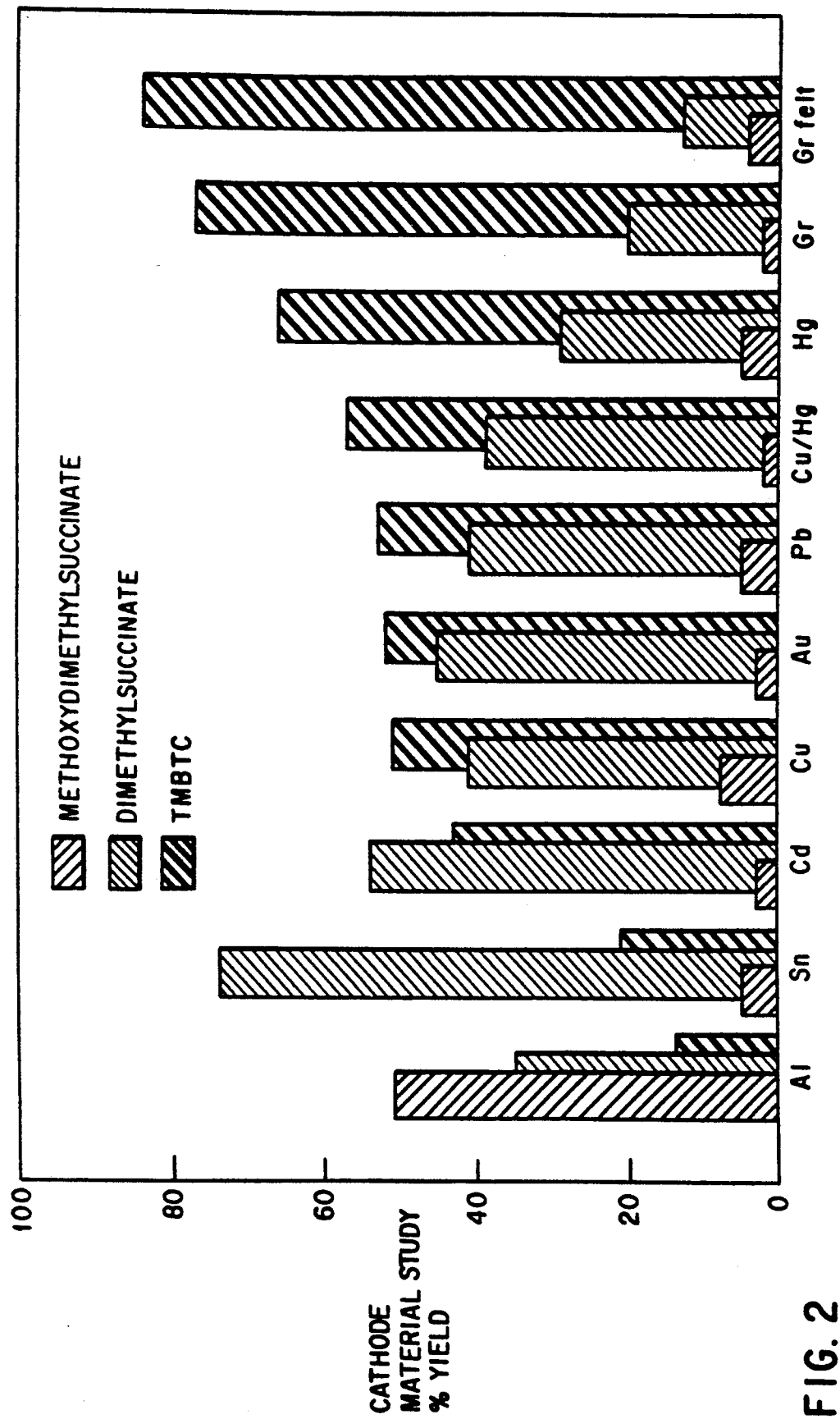
FIG. 2 is a drawing with bar graphs illustrating yields of tetramethyl butanetetracarboxylate and other products obtained by electrolysis in methanol employing various cathodes.

Electrolysis was conducted as in Example 5, with sodium acetate as electrolyte, and employing various cathodes. The selectivities obtained for the three major products are illustrated in the bar graphs of FIG. 2.

Example 7

A large flow cell was utilized to prepare tetramethyl butanetetracarboxylate in an electrolysis with sodium acetate as electrolyte. The cell was a modified Electro Syn Cell, (Svenska Utveklingsaketbologet, Swedish National Development Company) with 8 cells, later modified to 16 cells. The cell had 500 $cm^2$ graphite plates with about 1 mm spacing and plastic screens between electrodes to aid in flow dispersion. The cell was attached by polyvinyl chloride piping to a centrifugal pump, 18.93 liter (5 gallon) reservoir and stainless steel heat exchanger. The system was charged with about 8 kg dimethyl maleate, 15 kg of methanol and 200 g sodium acetate. The solution was circulated through the cell at about 75.7 liters (20.0 gallons) per minute. The cell was operated at 12.5 amperes (65-90 volts) for about 7.5 hours (with 16 cells). Typical analysis of the resulting solution was 25% tetramethyl butanetetracarboxylate, 5% L dimethyl succinate, 5% methoxydimethylsuccinate, 5% dimethyl maleate, and the balance methanol.

To describe in more detail, the cell had been modified to operate in a bipolar mode with only the end plates attached to the electrical supply. Stated quantities (reported in Table 4 below) of dimethyl maleate, methanol and sodium acetate were charged into the reservoirs as listed under DMM, MeOH and NaOAc. The circulation pump was activated and circulation was effected to achieve sample homogeneity, at a flow rate of 75.7 liters–79.5 liters (20–21 gallons) per minute. A sample was drawn at time zero, with DMM usually below charge quantity because of dilution by residue of a previous run. The power supply was activated and electrolysis conducted at 25 $mA/cm^2$ until the power was shut off at reported times. A sample was drawn and analytical results reported as %'s of reaction mixture, along with the selectivities to the products determined therefrom, and the grams of DMM which had reacted. Results of three different runs are reported in Table 4. Product selectivity as high as 83% was obtained in the third run, and thus, like the other runs in methanol, was carried to a high conversion, the conversion of dimethyl maleate being over 95%, based on the maleate in the product sample analysis, and the amount of reacted maleate A comparison of Run 1 with an 8 cell electrolysis, to Runs 2 and 3 with 16 cell electrolysis, shows that increasing the cells can cut the reaction time and also cut the amount of methoxydimethyl succinate product, thereby improving selectivity to the desired hydrodimer. In general the production of the by-product, produced by a chemical reaction, can be lessened by operating with a high electrolysis cell through-put compared to reservoir capacity, or other means to cut reaction time, as well as by limiting payload or lowering reaction temperature.

TABLE 4

| Run | Temp °C. | DMM g | MeOH g | NaOAc g | Time hr | PROD. MIX. ANAL., % | | | |
|---|---|---|---|---|---|---|---|---|---|
| | | | | | | DMM | MeOH | DMS | MeODMS |
| 1 (8 cells) | 23.0 | 9515 | 12950 | 200 | 0.0 | 37.0 | 59.3 | 0.6 | 2.7 |
| | | | | | 14.1 | 1.9 | 54.9 | 4.8 | 11.4 |
| 2 (16 cells) | 21.3 | 8230 | 13000 | 200 | 0.0 | 38.6 | 62.3 | 0.2 | 1.1 |
| | | | | | 7.3 | 2.2 | 61.3 | 5.4 | 5.3 |
| 3 (16 cells) | 20.1 | 8020 | 14810 | 200 | 0.0 | 33.5 | 66.3 | 0.7 | 1.0 |
| | | | | | 7.3 | 1.4 | ? | 3.5 | 4.0 |

| Run | PROD. MIX. ANAL., % TMBC | SELECTIVITIES, % | | | CONVERSIONS % DMM |
|---|---|---|---|---|---|
| | | TMBTC | DMS | MeODMS | |
| 1 | 2.2 | | | | |
| (8 cells) | 25.8 | 73.1% | 10.2% | 16.7% | 96.1 |
| 2 | 0.7 | | | | |
| (16 cells) | 28.8 | 77.6% | 13.7% | 8.7% | 95.1 |
| 3 | 2.7 | | | | |

TABLE 4-continued

| (16 cells) | 21.7 | 83.1% | 9.0% | 8.0% | 95.9 |

HYDROLYSIS OF TETRAALKYL BUTANETETRACARBOXYLATES

Example 8

To a 1-liter flask was added 43.8 g (0.151 mole) of tetramethyl 1,2,3,4-butanetetracarboxylate, 589.3 g of deionized water, and 0.79 g (6.8 mole) of phosphoric acid. The flask was fitted with a mechanical stirrer and a distillation head. The flask was heated and a mixture of water and methanol distilled overhead. The conversion was followed by analyzing for the amount of methanol collected. An additional 408.9 g water was added at 2.75 hour. An additional 2.37 g of 85% phosphoric acid was added at 4.2 hour. At 7 hours 389.7 g of water was added. The reaction mass was again heated at reflux overnight. Distillation was later continued. At 50.3 hours an additional 254.8 g of water was added. Distillation was stopped at 54 hours. At this time the cumulative methanol analyses indicated an 86% conversion of the esters to the free carboxylic acids. The pot reaction mass temperature through all but the first 20 minutes was 100° C.

The procedure described above was fragmented, over several work days, due to the long reaction time caused by the low reactivity of the tetramethyl-1,2,3,4-butanetetracarboxylate. Essentially, the reactor charge consisted of 6.9 wt % tetramethyl-1,2,3,4-butanetetracarboxylate, 0.5% phosphoric acid, and 92.6% water. Methanol was continuously distilled from the reactor as a methanol and water distillate. Water was added to replace the distillate. The reaction temperature was 100° C. Under these conditions the conversion of ester to free acid was 90% complete in 54 hours. This procedure is summarized in Table 5 as Example #8.

Example 9

Benzenesulfonic acid was used as the hydrolysis catalyst. To a 1-liter four-neck flask was added 28.5 g of TMBTC, 502.2 g of deionized water and 6.6 g of benzenesulfonic acid consisting of a 1.1 g initial charge, a 2.2 g addition after 1.1 hours, and a 3.3 g after 2.5 hours. The methanol was stripped as it formed. Water was added at 1.05 hours and 2.25 hours into the run at amounts of 423.6 g and 403.0 g respectively. Three distillation cuts were collected. These were a 316.6 g cut at one hour, a 450.9 g cut at 2.2 hours, and a 520.6 g cut at 3.6 hours. At this point the reaction was discontinued. Analysis of the cuts found that the reaction was 60% completed after 3.6 hours.

Example 10

Sulfuric acid was used as a hydrolysis catalyst. To a 500 ml four-neck flask fitted with a distillation head and condenser, and an addition funnel was added 68.4 g (0.235 mol) of tetramethyl 1,2,3,4-butanetetracarboxylate and a 129.5 g of water. This mixture was heated to 100° C. Then 20.6 g of concentrated sulfuric acid (95.5%, 0.201 mol) was added. Throughout most of the run the pot temperature was 103° C. The methanol formed by the reaction and some water was continuously stripped from the reactor. Water was continuously added to maintain a constant mass in the reactor. The reaction was 99.8% completed after 5 hours.

Example 11

The hydrolysis reaction of Example 10 was repeated but with less sulfuric acid catalyst. The reactor charges were 68.7 g (0.236 mol) of the tetraester and 142.8 g of water. This mixture was heated to 100° C. Then 6.73 g of concentrated sulfuric acid (95.5%, 0.065 mol) was added. The procedure was carried out in the same way as the above example that used 20.6 g of acid. A 97.0% conversion was obtained in 8.5 hours at 101° C. The example using 20.6 g achieved a 97% conversion in 3.1 hours. In the present example, conversion Was only about 94% at 6.5 hours.

Example 12

The conditions of Example 10 were repeated except that the temperature of the reaction mass was maintained at 80° C. by controlling the pressure at 54.0 kPa (405 torr) to 58.7 pKa (440 torr). The equipment described in the preceding examples was charged with 68.4 g (0.236 mol) of tetramethyl 1,2,3,4-butanetetracarboxylate, and 129.4 g of water. The mass was heated to 78° C. Then 20.4 g of concentrated sulfuric acid (95.5%, 0.199 mol) was added. The reactor pressure was adjusted to maintain an 80° C. reaction temperature. This reaction was 94% completed in 9.4 hours. The same experiment but at a 103° C. reaction temperature achieved a 94% conversion in 2.7 hours.

Example 13

Hydrolysis was conducted in accord with the procedure of Example 1, but utilizing 10.3 (0.100 mol) of 95.5% sulfuric acid. A reaction time of 5 hours gave a 94.7% conversion.

TABLE 5

| Exp # | TMBTC Grams | Moles | $H_2SO_4$ Grams | Initial Water Grams | Added Water Grams | Reac Time Hours | Reac Temp. °C. | Conv. % |
|---|---|---|---|---|---|---|---|---|
| 8 | 43.8 | 0.151 | 3.2* | 589.3 | 1740.7 | 54.0 | 100 | 90.5 |
| 9 | 28.5 | 0.0982 | 6.6** | 502.2 | 826.6 | 3.6 | 102 | 60.0 |
| 10 | 68.4 | 0.235 | 20.6 | 129.5 | 685.1 | 5.0 | 103 | 99.8 |
| 11 | 68.7 | 0.236 | 6.73 | 142.8 | 1485.8 | 8.5 | 101 | 97.0 |
| 12 | 68.4 | 0.236 | 20.4 | 129.4 | 1669.7 | 9.4 | 80 | 93.3 |
| 13 | 68.5 | 0.236 | 10.3 | 139.3 | 623.1 | 5.0 | 102 | 94.7 |

*phosphoric acid as catalyst
**benzenesulfonic acid as catalyst

Figure 3:
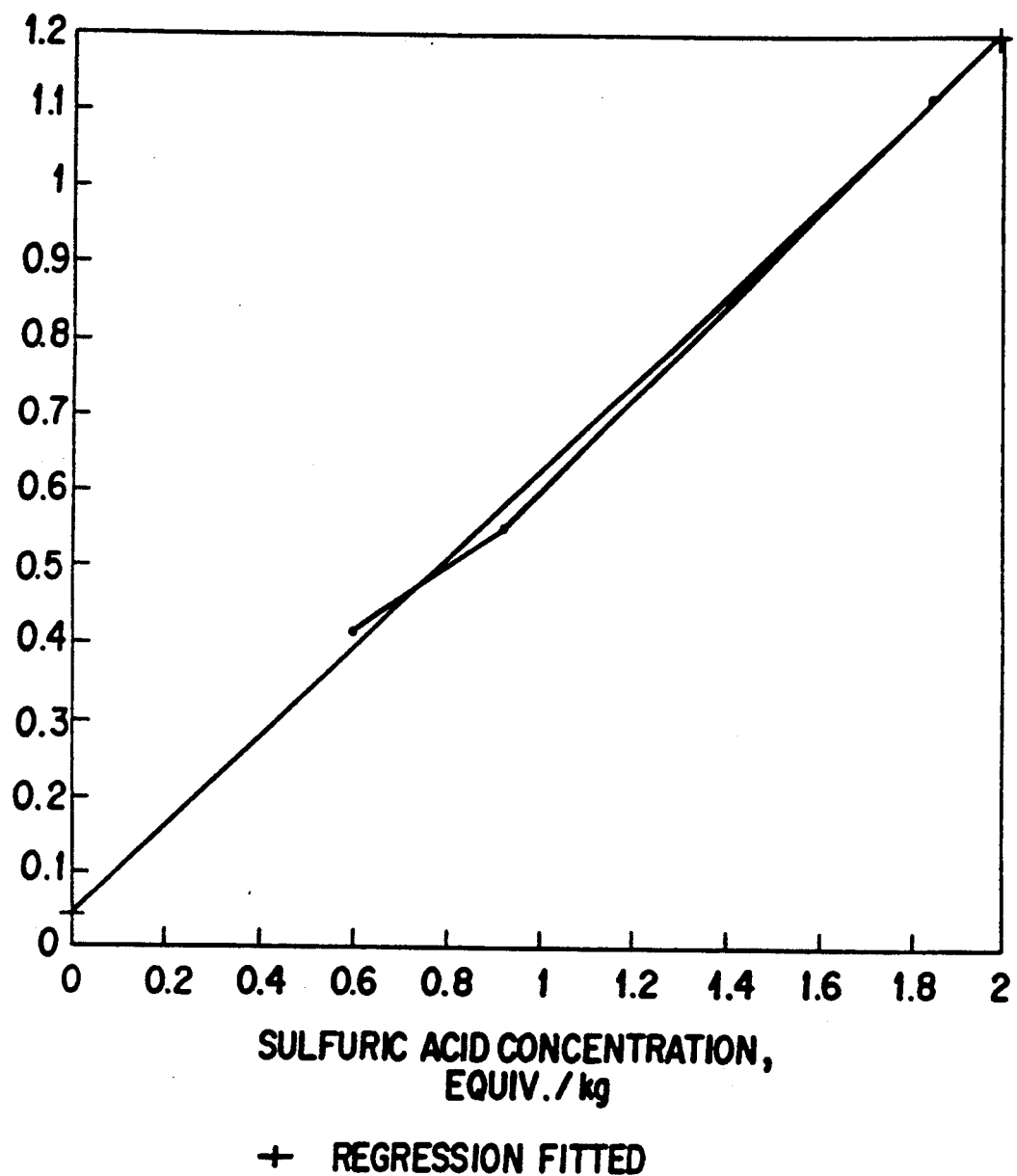
FIG. 3 is a graph of TMBTC hydrolysis rate constant vs. acid concentration.

In Examples 8 and 9 of the Table, large amounts of water and low acid concentrations were used, as often employed in typical hydrolysis reactions, and very slow reactions resulted in Example 10 a lower amount of water and high concentration of acid was used, providing about 1.83 gram-equivalents acid per kg. of reaction mixture, and a much faster reaction was obtained. In Example 11 the acid concentration was still fairly strong, but much lower than that in Example 10 with a corresponding drop in reaction rate. From the reaction rates of Examples 10, 11, and 13, rate constants for the reaction were plotted against sulfuric acid concentration, as illustrated in FIG. 3. It can be seen that the rate increases in essentially a straight-line relationship with increase in acid concentration. The results fit (by regression fit) the relationship:

$$K = 0.580638 \text{ (gram-equiv. } H_2SO/kg) + 0.045685$$

There is advantage in using a high enough acid concentration to get a good reaction rate, such as at least 1 gram equivalent $H_2SO_4$ per kg. of reaction mixture, and a rate constant of at least 0.6 hour $-1$, and reaction rates sufficient to complete a batch reaction within about 6 hours. It will be preferred to utilize acid concentrations of more than 1.5 gram-equivalents acid per kg reaction mixture.

Figure 4:
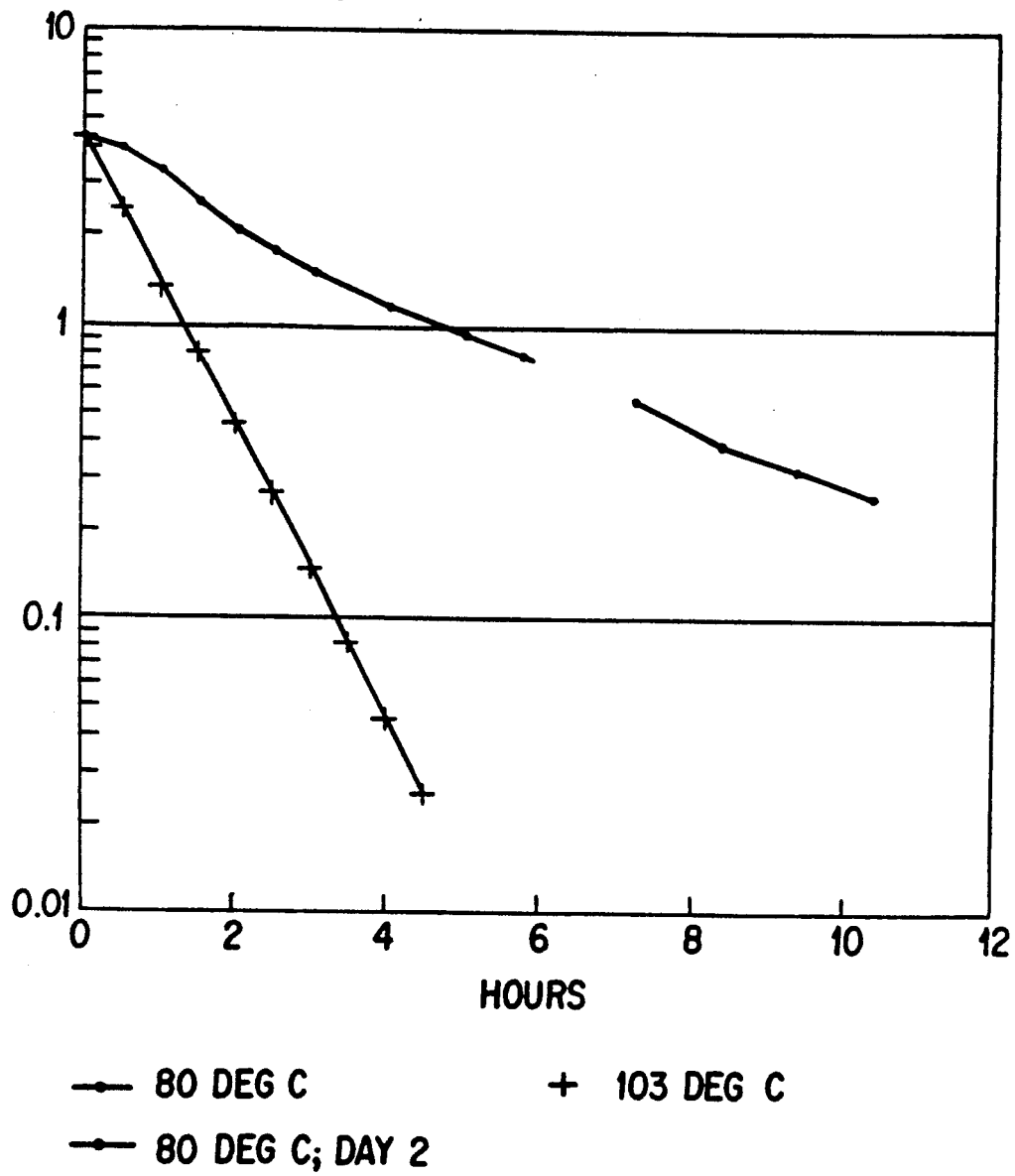
FIG. 4 is a graph showing TMBTC hydrolysis vs. time at different temperatures.

In FIG. 4 hydrolysis reactions at two different temperatures (Examples 10 and 12 above) are plotted in terms of equivalents of unhydrolyzed ester per kg of reaction mixture vs. reaction time. The results on semi-log paper show a consistent decline in both cases, with the reaction at 103° C. (Example 10) being essentially complete in slightly more than four hours, while that at 80° C. (Example 12) was far from complete after 10 hours, with a trend indicating a much longer time would be needed for completion. These results indicate it is very important to use a relatively high reaction temperature, such as upwards of 95° C., or near or over 100° C., in order to have a good reaction rate. Hydrolysis under pressure at temperatures over 100° C. would be desirable.

Figure 5:
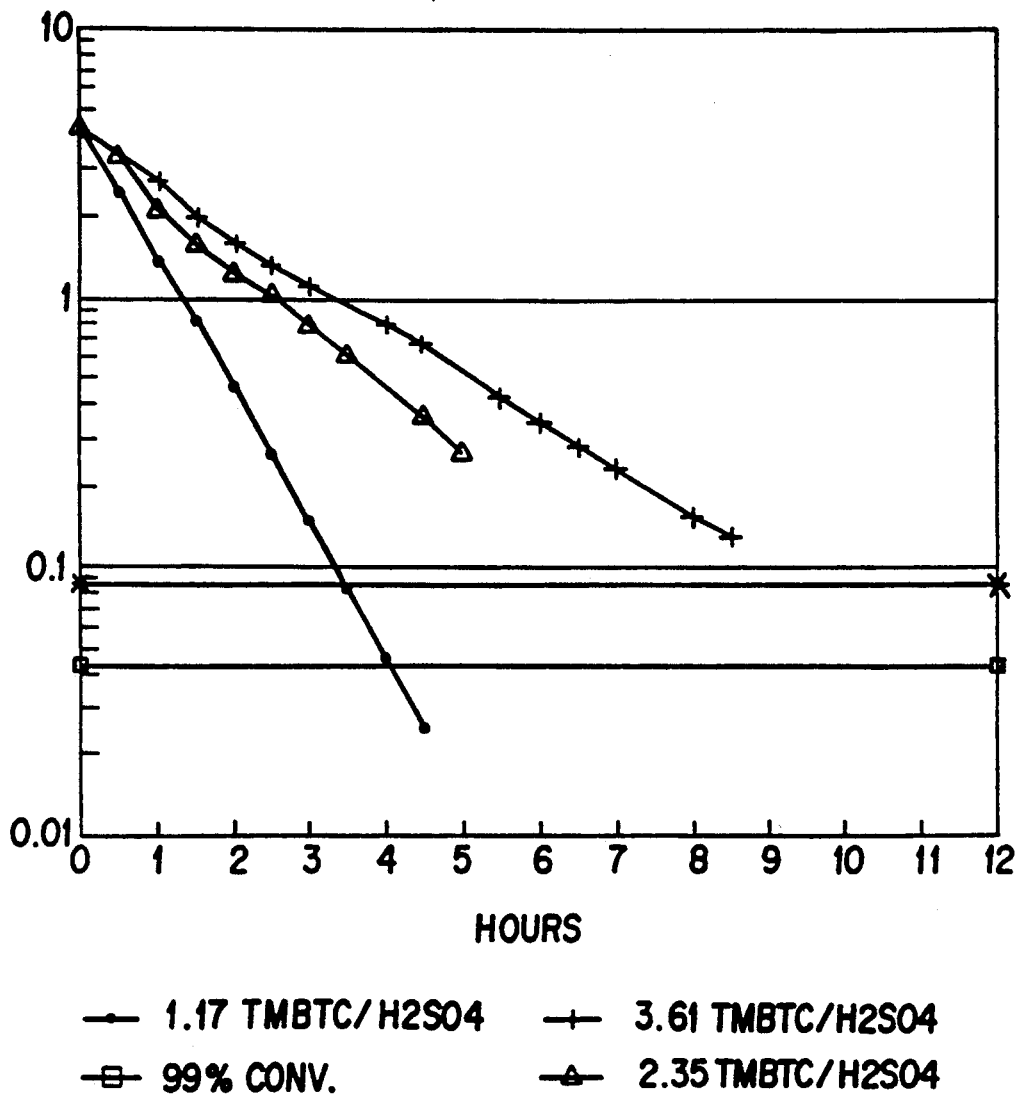
FIG. 5 is a graph showing TMBTC hydrolysis vs. time for different TMBTC/$H_2SO_4$ mole ratios.

In FIG. 5, hydrolysis results of Examples 10, 11, and 13 are plotted on semi-log paper for reactions employing different mole ratios of TMBTC to $H_2SO_4$, the ratios being 1.17 (Example 10), 3.61 (Example 11) and 2.3 (Example 13). The reaction with the 1.17 TMBTC/$H_2SO_4$ ratio was essentially complete within 5 hours, while the other reactions were slower with the trend of the 3.61 TMBTC/$H_2SO_4$ reaction indicating over 9 hours to reach the 97% conversion line (the line marked by asterisks below the 0.1 line). These results indicate advantage in using relatively low TMBTC/$H_2SO_4$ mole ratios, such as not over about 2.

Good reaction rates and short reaction times have the advantage of permitting good production rates with the equipment employed. An additional consideration is that batch runs of less than 8 hours, such as less than 6 hours, are very advantageous for fitting into normal work schedules. The hydrolysis reaction mixture with TMBTC as reactant involves water and methanol, so 103° C. is about the highest temperature obtainable during most of the reaction, although temperatures up to 111° C. or so are obtained as methanol and some water are removed in the later part of the reaction. Higher temperatures could be obtained by employing pressure or possibly by regulating the components. The amount of methanol in the reaction mixture affects the reaction temperature, possibly keeping it at 100° C. or so if methanol is permitted to build up before being removed by distillation. Accordingly, it is advantageous to provide heating sufficient to distill methanol from the reaction mixture at a good rate. The presence of methanol also tends to retard the reaction, since it is a product in an equilibrium reaction, and this is an additional reason for removing it. In the distillation water is also removed at a relatively high rate and replaced by additional water to provide water for the reaction. The total water supplied in the hydrolysis procedure is generally at least four times the amount present on the average during the hydrolysis procedure.

A sample of BTCA will ordinarily contain some color-causing materials. These materials may be color bodies which actually give the BCTA a color, ordinarily yellow; or materials which form color when the BCTA is heated. For test purposes, color was developed in samples by heating in a vacuum oven for at least 24 hours. Color-causing materials can be neutralized or removed to a great extent by a peroxide treatment. The treatment procedure involves adding a small amount of hydrogen peroxide to the BCTA hydrolysate solution and agitating at moderately elevated temperature, e.g. 55° C. for a short time, sufficient for reaction, such as 30 minutes or more. The mixture is then heated to reflux, ordinarily about 106° C., to decompose excess peroxide and peracids. It is contemplated that this can be accomplished in about 30 minutes, but may take much longer, a number of hours, in the absence of metal contaminants or other materials to catalyze the decomposition.

Example 14

In this Example, a peroxide treatment, following a hydrolysis of TMBTC, is described. To a 500 ml four-neck flask was added 86.2 g (0.297 mol) of TMBTC and a mixture of 26.0 g (0.265 mol) of concentrated (95.5%) sulfuric acid in 163.3 g of water. This mixture was mechanically stirred and heated to effect a hydrolysis of the tetraester. A mixture of methanol and water was continuously distilled from the flask. Water was added to the flask to maintain a constant mass. After 7.5 hours the hydrolysis was completed. There was recovered 161.6 g of a light yellow hydrolysate solution containing the BTCA. A 100.0 g aliquot of the hydrolysate solution was returned to the 500 ml flask. To the hydrolysate was added 1.02 g of 30% hydrogen peroxide ($H_2O_2$). The solution was slowly heated to a reflux temperature of 110° C. The solution was frequently tested for the presence of peroxides with starch-iodide paper. The solution gave a negative test after 9.75 hours of refluxing. The heating to reflux in the procedure was slow enough to allow considerable time for reaction in the 50 to 60° C. range.

CHARACTERIZATION OF BUTANETETRACARBOXYLIC ACID

Example 15

A number of different samples of BCTA were appraised for color in accordance with the following test. The parameters and results are reported in Table 6.

The color level of the BTCA samples was appraised by spectrophotometry. Some samples were heated as solids to 89° C. prior to testing. Color determinations were made on 10% solutions of samples in either aqueous KOH, or deionized water. The UV/visible spectrum (200 nm to 800 nm) was obtained for each sample using an HP8451A diode-array spectrophotometer. An absorbence measurement was recorded at a single wavelength, 400 nm, in the visible region. While color is the sum of many wavelengths, the absorbance at 400 nm provides a secondary measurement of the color of each solution. Also, BCTA alone does not absorb light at 400 nm

TABLE 6

Absorbance at 400 nm of BTCA water solutions.

| Sample Description | Hydrogen Peroxide Treated | Heated at 89° C. | 400 nm Absorbance | Factor |
|---|---|---|---|---|
| Laboratory BTCA | Yes | No | 0.01094 | 1.0 |
| Pilot Plant BTCA after neutralization of $H_2SO_4$ | Yes | Yes | 0.016891 | 1.5 |
| Pilot Plant BTCA recrystallized from water | No | Yes | 1.42019 | 125 |
| Pilot Plant BTCA containing residual $H_2SO_4$ | Yes | Yes | 0.886947 | 78 |
| Laboratory Prepared BTCA | No | No | 0.02745 | 2.4 |
| Laboratory BTCA TMBTC not water extracted | Yes | Yes | 2.01533 | 184 |
| Laboratory BTCA TMBTC extracted once with water | Yes | Yes | 0.274368 | 25 |
| Commercial BTCA #1 | No | No | 0.021621 | 1.9 |
| Commercial BTCA #1 | No | Yes | 0.043579 | 3.8 |

In Table 6, BCTA from this process was used to provide a base line and assigned a Factor of 1. The other Factors are calculated from the ratio of a sample's absorbance, compared to the base line BCTA. The results with pilot plant BCTA show that marked improvement can be obtained by either recrystallization, or peroxide treatment, or neutralization of residual sulfuric acid. The results with laboratory prepared BCTA show that marked improvement is obtained by peroxide treatment. The benefit of the water extraction of TMBTC is also demonstrated. The results also indicate that color purity can be obtained better than that of a commercial sample, with the sample after neutralization of sulfuric acid having only 40% of the absorbance of a commercial sample subjected to the same heat treatment. The commercial sample, #1 (Aldrich Chemical), is presumed to be a product obtained by oxidative cleavage of tetrahydrophthalic anhydride. The above results clearly demonstrate the beneficial effect of peroxide treatment. However, it should also be noted that, aside from the above results, some of the above and other samples, from the present process, exceed performance specifications for permanent press agents and may be better in performance than other available candidates. With regard to the pilot plant BTCA, the material contained more impurities than is apt to be typical of the pilot plant product. A poor separation was obtained in the filtration of the precursor TMBTC, and better filtration and separation is obtainable.

The laboratory prepared BTCA was prepared on a laboratory scale by a process involving the same steps as described for an exemplary pilot plant process herein, but with variations noted in Table 6; also, an acid neutralization step was not used.

It was found that pilot plant BTCA, as expected from aqueous solution by filtration, contained residual $H_2SO_4$. Titration with NaOH solution was utilized to determine the $H_2SO_4$ quantitatively, so it could be neutralized. A sample of commercial BTCA (Aldrich Chemical) as a 12% solution was determined to have a pH of 1.68 at 25° C., 1.76 at 24° C., and 1.85 at 22° C. Titration of a 12 wt % solution of pilot plant wet cake found that the material contained 4.06 wt % sulfuric acid. A 785.6 g sample of pilot plant BTCA was slurried in a flask with 202 g deionized water. The calculated 31.88 g $H_2SO_4$ content would require 26 g NaOH for neutralization. A 51.4 gram quantity of a 50% solution of NaOH was slowly added to the stirred slurry at 80° C. to provide a stoichiometrically equivalent amount of sodium hydroxide. The slurry was cooled to 35° C. and filtered, affording 436.3 g of BTCA crystals. The pH of a 12% solution of the caustic treated BTCA crystals was 1.80 at 24° C. The material is referred to as "after neutralization" in Table 6 above, as "Finished BTCA" in Table 7 below, and "Monsanto BTCA" in Table 8 below. A slurry is preferable to a solution for the neutralization, in order to avoid high yield losses due to the solubility of the BTCA. In commercial production it will be desirable to recycle the filtrate to subsequent batch neutralization procedures in order to lower BTCA losses.

Example 16

An alternate procedure was utilized to appraise color development of BTCA samples upon heating. In this procedure 10 grams of BTCA was dissolved in 93 grams of ethylene glycol and the solution was refluxed at 198° C. for 24 hours. The absorbance at 400 nm was then measured. Results are reported in Tables 7 and 8. Ethylene glycol was used to provide a base line; it was assigned a Factor of 1.

TABLE 7

Heat Discoloration Test
Effects of the Various Processing Steps

| Sample | $H_2O_2$ Treated | 400 nm Absorbance Factor | |
|---|---|---|---|
| | | Before Heating | After Heating |
| 1. Ethylene Glycol | | | 1.0 |
| 2. Finished BTCA | X | 1.4 | 6.3 |
| 3. W/O neutralization of $H_2SO_4$ | X | 4.2 | 8.1 |
| 4. W/O $H_2O_2$ treatment | | 4.8 | 8.5 |
| 5. W/O water extraction of TMBTC | X | 5.1 | 12.7 |

Table 7 shows the effect of various processing steps. It is apparent that omission of any of the steps results in more color, both before and after the samples are heated.

TABLE 8

Heat Discoloration Test
BCTA in Ethylene Glycol[1]

| Sample | $H_2O_2$ Treated | 400 nm Absorbance Factor | |
|---|---|---|---|
| | | Before Heating | After Heating |
| 1. Ethylene Glycol | | | 1.0 |
| 2. Aldrich BTCA | | 7.99 | 21.5 |
| 3. Aldrich BTCA | X[2] | 13.2 | 9.7 |
| 4. Commercial BTCA #2 | | 3.7 | 10.0 |
| 5. Monsanto BTCA | | 4.8 | 8.5 |
| 6. Monsanto BTCA | X | 1.4 | 6.3 |

[1]Heated at 198° C. for 24 hours.
[2]Treated in the laboratory following purchase.

In Table 8 Monsanto BTCA prepared by the present process, both with and without peroxide treatment, is compared to commercial samples. The Monsanto BTCA #6, a finished BTCA with peroxide treatment, is superior to the commercial samples, and also shows advantages over a Monsanto sample which had not been peroxide treated. The commercial BTCA #2 is a commercial sample of unknown source. The reference to Aldrich BTCA as peroxide treated refers to a treatment carried out and reported in Table 8, rather than indicating that the material as available commercially has been peroxide treated.

Example 17

Figure 6:
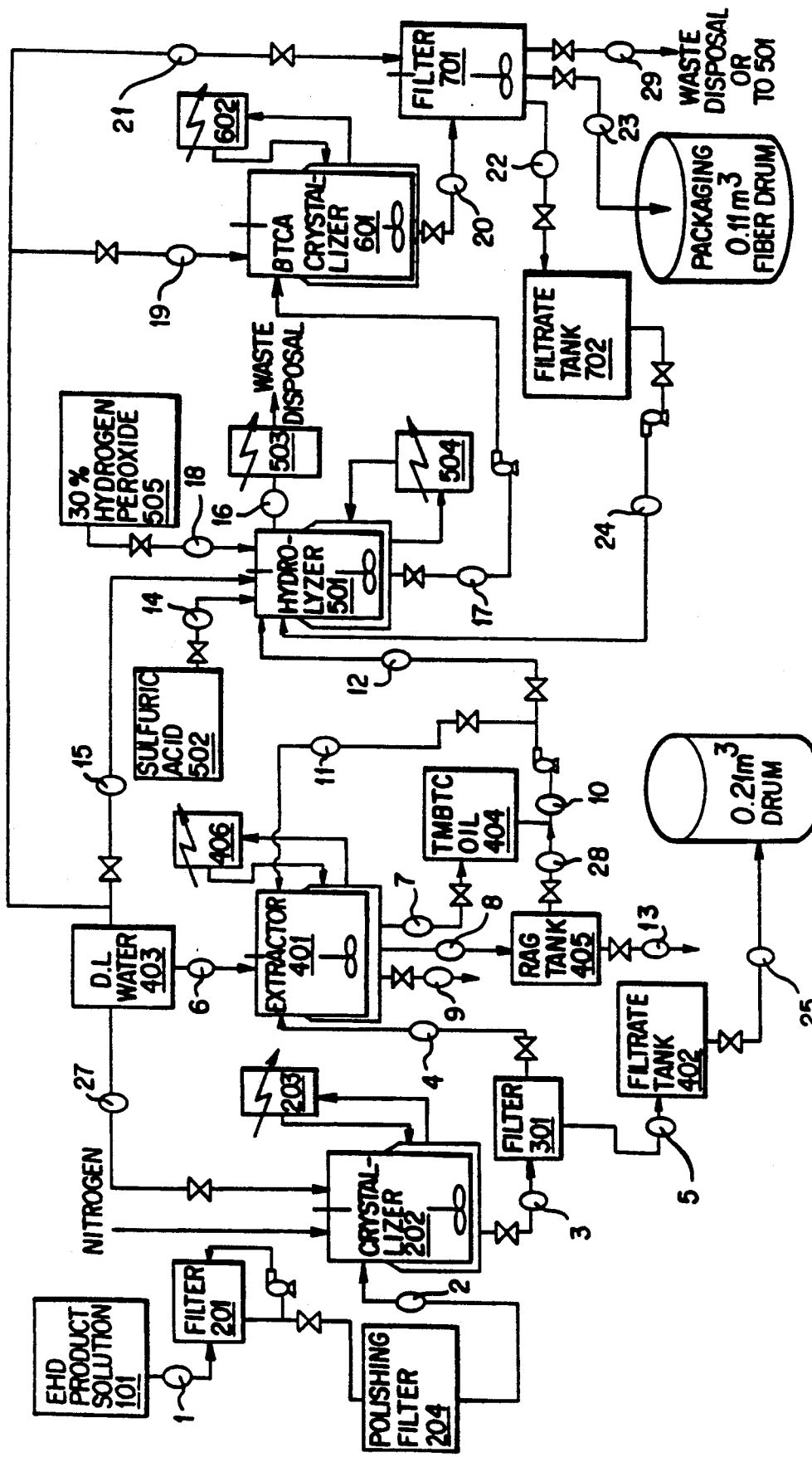
FIG. 6 is a flow sheet for an exemplary process for preparing BTCA.

The drawing, FIG. 6, is a process flow-diagram illustrating the various unit processes and flow streams involved in preparing butanetetracarboxylic acid from tetramethyl butanetetracarboxylate in accord with an exemplary embodiment of the present invention.

The present process is especially useful for preparing butanetetracarboxylic acid from tetramethyl butanetetracarboxylate obtained as product in an electrohydrodimerization, as described herein. The tetramethyl butanetetracarboxylate (TMBTC) from an electrohydrodimerization (EHD) will ordinarily be provided as a methanol solution, containing for example 24–25% by weight of TMBTC. To describe the process in accord with FIG. 6, the solution of TMBTC in feed storage tank 101 is pumped as stream 1 through a filter 201 and a polishing filter 204 and stream 2 to crystallizer 202. The TMBTC solution as provided contains small amounts of black particulates, presumably graphite from electrode erosion in the EHD cells. The particulates can cause formation of a rag layer during an extraction step which is part of the present process and separation of oil and water phases in the extraction is greatly improved by prior removal of particulates. The separation requires much less time in the substantial absence of particulates, so the filtration is clearly advantageous when particulates are present. Of course, the filtrations would not be very useful if particulates were not present, as might be the case if the TMBTC were prepared in a process using metal electrodes, or in a process other than an EHD process. In the filtration the first filter, 201, is used to remove the particulates, for example by employing diatomaceous earth by adding it to feed storage tank 101, which is stirred to maintain a suspension. The intention is to provide sufficient diatomaceous earth to form about a 1.27 cm layer on the filter cloth in filter 201. The filtrate from 201 is pumped back to filter 201 until a clear filtrate is observed, which is then pumped forward to polishing filter 204, which is preferably equivalent to 6 microns or finer filter paper, and then to crystallizer 202.

The filtered solution contains, for example, about 25% by weight TMBTC. The TMBTC is crystallized from the solution by cooling to near $-10°$ C. while stirring. Crystallization will occur at 0° C. or below, but the amount recovered increases markedly as the temperature is lowered from 0 to $-10°$ C. There is still some further improvement below $-10°$ C., but this is offset by the increasing cooling costs and time to achieve the cooling with available refrigeration means. Ordinarily a temperature of about $-10°$ C. will be preferred, but temperatures of $-15°$ C. or $-20°$ C. or lower can be employed. At $-10°$ C., about 88% of the TMBTC crystallizes from solution.

The TMBTC recovery can be increased by adding water to the methanol solution containing TMBTC. The addition of water at about three times the weight of the solution, i.e. to have about 75% water, improves the TMBTC recovery at $-10°$ C. to about 98%, and also partitions more of the solution components into the filtrate. However, 75% water uses a large volume in the crystallizer vessel, and it will probably be expedient to use a lesser amount of water, say 25%, and accept a somewhat lower recovery, say 93% or so.

The crystallizer 202 is maintained under nitrogen as a precaution, in view of the flammability of methanol.

The mixture of crystals and liquor from the crystallizer is sent by stream 3 to filter 301, where the crystals are separated from the liquor. The crystals are then melted by heating to a temperature of about 75° C., or higher, and the melt is forwarded as stream 4 to extractor 401. In the extractor deionized water from tank 403 as stream 6 is mixed with the melt and then separated into water and oil phases in order to remove salt and other water solution components. The temperature in the extractor is kept at about 70°–76° C. to avoid solids formation. TMBTC melts in a range of about 55°–60° C., but the meso-isomer has a melting point of 76° C. Temperatures to avoid solids formation are preferable. The extraction will usually employ about equal weight parts TMBTC and water, e.g. to 171 parts TMBTC, 175 parts water is added with heating to 75° C., and agitation is started and continued for about 30 minutes. Agitation is stopped, and phase separation commences. A particulate-free mass separates in minutes at 75° C., but generally some particulates are present and a rag layer will form between a lower oil TMBTC layer and an upper water layer. A typical separation is 17.9 parts of rag layer, 141.9 parts of lower oil layer and 184.6 parts of upper water layer. The lower oil layer is sent by stream 7 to TMBCT oil hold tank 404. The rag layer as stream 8 is stored in a tank 405 where the rag will slowly separate, and the oil may be recovered as stream 28 and returned to the extractor, or it can be slowly isolated and periodically added to hydrolyzer 501 while water is disposed of in stream 13. The water layer in extractor 401 contains about 1% TMBTC, and is collected from stream 9 for disposal. The oil layer from 404 is returned to the extractor by stream 11 and the extraction is repeated, using, for example, 147 parts of deionized water. The TMBTC oil layer from 404, about 136.8 parts, is then sent via streams 10 and 12 to hydrolyzer 501. The hydrolyzer is a jacketed, glass-lined vessel provided with an agitator and condenser, and equipped with ample heating means. The hydrolysis is conducted with an amount of water of only about twice the weight of the TMBTC, and a high concentration of mineral acid catalyst. Also, methanol is distilled from the reaction mixture in order to drive the reaction. To 136.8 parts of TMBTC, 127 parts of water is added through stream 15 and agitation is started. A charge of 38.1 parts sulfuric acid is added, from two sources, the BTCA crystallizer filtrate tank, 702, and make-up from sulfuric acid bottles, 502. To provide the acid, the hydrolyzer is charged with 203 parts of solution from the tank 702 through stream 24 and 1.1 parts of new sulfuric acid from bottles 502 through stream 14. In addition to sulfuric acid, the filtrate also provides the BTCA heel from the BTCA crystallization and separation, with the use of the heel providing a near stoichiometric recovery of the BCTA. The BCTA filtrate contains 17% by weight BCTA at ambient temperature. The hydrolysis may be completed by about 4.5 hours reaction with simultaneous stripping of methanol, or by refluxing until equilibrium is reached, followed by stripping of methanol. In the latter procedure, about 76% hydrolysis is achieved in 1 hour, and this is followed by distillation of methanol and water for about 3 hours, with addition of water in amount to replace distillate. An appropriate addition rate maintains a pot temperature of 103.5° C. However, at the beginning of the distillation the pot temperature is depressed by the high concentration of methanol, and water is added at 5.57 parts per minute until the temperature reaches 103.5° C. After three hours of distillation, the water addition is stopped and distillation continued until the pot temperature reaches 111° C. The hydrolyzer distillate at 503 can be disposed of, being water and a small concentration of methanol. The hydrolysis mass in the hydrolyzer 501 will contain some color or color-forming bodies. These can be greatly reduced by a simple oxidation procedure. An oxidizing agent which will oxidize the color and color-forming bodies, and not leave objectionable amounts of color-causing contaminants, is appropriate for use. It has been found that hydrogen peroxide serves very well. The reaction with hydrogen peroxide is performed in the hydrolyzer 501 after the hydrolyzed solution is cooled to a temperature of between 45 and 55° C. To the hydrolyzed solution present in about 308 weight parts, a charge of 2.5 parts of 30% hydrogen peroxide in water is added from container 505 through stream 18. The solution is agitated for about 30 minutes at 45°-55° C. Then the temperature is increased and the solution is refluxed for about 30 minutes or as necessary to decompose excess peroxide and such peracids as present. The absence of peroxides and peracids is determined by testing with acidified starch-iodide paper.

A 310.7 parts amount of hydrolyzed and oxidized reaction mass from hydrolyzer 501 is pumped as hot liquid through a stream 17 to BCTA pumped as hot liquid through stream 17 to BTCA crystallizer 601. The crystallizer is a glass-lined tank equipped with cooling and agitation. The liquid is cooled to about 22° C., by tower water, and product allowed to crystallize. When crystallization appears complete, the 310.7 parts of crystallization mass is transferred as stream 20 to filter 701. The aqueous sulfuric acid filtrate is corrosive, and therefore the filter will be of corrosion resistant materials. A suitable filter medium is, for example, 3-6 micron screen or filter paper. The crystallizer mass separates into 105 parts of BTCA crystals and 202 parts of filtrate. The filtrate is sent as stream 22 to tank 702 for recycle as stream 24 back to the hydrolyzer as catalyst and heel. In a crystal washing step, 24.7 parts of deionized water is added by stream 21 to the filter and the BTCA re-slurried. The resulting 30 parts of filtrate is preferably directed to filter tank 702, or alternatively as stream 29 for waste disposal. The BTCA crystals are optionally dried by warm air, or may be packaged for shipment with water analysis being reported. In repeated production runs, it is anticipated that the filtrate from the BTCA will be recycled to the next batch filtration, thereby making the BTCA recovery near quantitative. The filtrate liquor contains approximately 16.5% BTCA. A problem with impurities may develop if corrosion occurs, or as by-products build up in the filtrate. If BCTA quality were affected, the problem could be minimized by removing a portion of the filtrate after each batch. If filtrate quality considerations require disposing of large portions of the filtrate, it will be desirable to use lower than ambient temperature for the BTCA crystallization in order to increase the percentage of BTCA which crystallizes. An alternative is to leave the BTCA in solution and to supply it for use in solution form.

As described hereinabove, BTCA produced in the present process may contain substantial amounts of residual acid catalyst. In a procedure (not illustrated in the Flow-Diagram of FIG. 6), the BTCA product can be treated with base to remove the acid by neutralization. It will generally be desirable to provide sufficient base, e.g. NaOH, to completely neutralize the acid. However, partial neutralization is also beneficial, so amounts of base stoichiometrically equivalent to or less than equivalent to the acid can be used. An excess of base can be used, but will tend to form salts with the BTCA, causing some loss due to aqueous solubility. In order to avoid unnecessarily large losses of BTCA yield due to solubility, it will be desirable to use only small amounts of water in the neutralization to form a slurry of the BTCA, into which a caustic solution can be stirred slowly. The BTCA is then filtered from the slurry in crystalline form.

Bases in general can be used for the neutralization, although solubility considerations may make some inconvenient. Alkali metal hydroxides, however, particularly sodium and potassium hydroxides, are convenient and readily available. Other known methods of removing acid contaminants can be used, including those involving ion exchange resins. In view of the relatively high solubility of BTCA in water, it will be desirable to save the filtrate for return to a subsequent neutralization batch, and to employ cooling for the separation, to ambient or possibly lower temperatures. In some applications for BTCA, the use will be in a controlled pH environment or otherwise involve neutralization of residual acid, so that neutralization is not needed as part of the BTCA preparation process.

Table 9 is a Materials Balance table setting forth the projected weight parts of various components in the streams of the flow-diagram of FIG. 6, when the present process is carried out in accordance with the flow diagram and the foregoing description, and supplying materials as indicated in the table. In the table, DMM stands for dimethyl maleate, DMS for dimethyl succinate, and MeO-DMS for methoxydimethylsuccinate.

TABLE 9

| COMPONENT | MW | STREAM | | | | | | | | | |
| --- | --- | --- | --- | --- | --- | --- | --- | --- | --- | --- | --- |
| | | 1 | 2 | 3 | 4 | 5 | 6A | 6B | 7 | 8 | 9A |
| BTCA | 234.16 | 0.0 | 0.0 | 0.0 | 0.0 | 0.0 | 0.0 | 0.0 | 0.0 | 0.0 | 0.0 |
| TMBTC | 290.27 | 147.8 | 147.8 | 147.8 | 133.5 | 14.3 | 0.0 | 0.0 | 129.8 | 0.2 | 1.7 |
| DMM | 144.13 | 10.2 | 10.2 | 10.2 | 0.0 | 10.2 | 0.0 | 0.0 | 0.0 | 0.0 | 0.0 |
| DMS | 146.14 | 29.2 | 29.2 | 29.2 | 2.4 | 26.7 | 0.0 | 0.0 | 1.5 | 0.0 | 0.8 |
| MeO-DMS | 176.17 | 16.2 | 16.2 | 16.2 | 0.0 | 16.2 | 0.0 | 0.0 | | | |
| MeOH | 32.04 | 367.6 | 367.6 | 367.6 | 34.4 | 333.3 | 0.0 | 0.0 | 5.1 | 8.8 | 20.5 |
| NaOAc | 82.03 | 5.8 | 5.8 | 5.8 | 0.5 | 5.3 | 0.0 | 0.0 | 0.0 | 0.0 | 0.5 |
| Water | 18.01 | | | 72.9 | 0.4 | 72.6 | 175.0 | 147.0 | 5.2 | 8.8 | 161.1 |
| $H_2SO_4$ | 98.08 | | | | | | | 0.0 | | | |
| $H_2O_2$ | 34.01 | | | | | | | 0.0 | | | |

TABLE 9-continued

| STREAM | | | | | | | | | | |
|---|---|---|---|---|---|---|---|---|---|---|
| Graphite | 12.01 | 0.0 | | | | | 0.0 | | | |
| Maleic Acid | 116.07 | | | | | | 0.0 | | | |
| Succinic Acid | 118.09 | | | | | | 0.0 | | | |
| Fumaric Acid | 116.07 | | | | | | 0.0 | | | |
| 2-MeO-Succinic Acid | 148.11 | | | | | | 0.0 | | | |
| TOTALS | | 576.8 | 576.8 | 649.7 | 171.2 | 478.6 | 175.0 | 147.0 | 141.7 | 17.9 | 184.6 |

| COMPONENT | 9B | 10 | 11 | 12 | 13 | 14 | 15 | 16 | 17 | 18 |
|---|---|---|---|---|---|---|---|---|---|---|
| BTCA | 0.0 | 0.0 | 0.0 | 0.0 | 0.0 | 0.0 | 0.0 | 0.0 | 138.3 | 0.0 |
| TMBTC | 1.7 | 130.0 | 130.0 | 130.0 | 0.0 | 0.0 | 0.0 | 0.0 | 0.0 | 0.0 |
| DMM | 0.0 | 0.0 | 0.0 | 0.0 | 0.0 | 0.0 | 0.0 | 0.0 | 0.0 | 0.0 |
| DMS | 0.0 | 1.5 | 1.5 | 1.5 | 0.0 | 0.0 | 0.0 | 0.0 | 0.0 | 0.0 |
| MeO-DMS | 0.0 | | | | 0.0 | 0.0 | 0.0 | 0.0 | 0.0 | 0.0 |
| MeOH | 5.1 | 5.1 | 5.1 | 0.0 | 8.8 | 0.0 | 0.0 | 56.8 | 0.0 | 0.0 |
| NaOAc | 0.0 | 0.0 | 0.0 | 0.0 | 0.0 | 0.0 | 0.0 | 0.0 | 0.0 | 0.0 |
| Water | 147.0 | 5.2 | 5.2 | 5.2 | 8.8 | 0.1 | 1464.0 | 1438.4 | 133.0 | 1.9 |
| H$_2$SO$_4$ | 0.0 | | | | | 1.1 | | | 38.2 | |
| H$_2$O$_2$ | 0.0 | | | | | | | | | 0.8 |
| Graphite | 0.0 | | | | | | | | | |
| Maleic Acid | 0.0 | | | | | | | | | |
| Succinic Acid | 0.0 | | | | | | | 1.2 | | |
| Fumaric Acid | 0.0 | | | | | | | | | |
| 2-MeO-Succinic Acid | 0.0 | | | | | | | | | |
| TOTALS | 153.8 | 141.9 | 141.9 | 136.8 | 17.6 | 1.2 | 1464.0 | 1495.2 | 310.7 | 2.8 |

| COMPONENT | 19 | 20 | 21 | 22 | 23 | 24 | 25 | 27 | 28 | 29 |
|---|---|---|---|---|---|---|---|---|---|---|
| BTCA | 0.0 | 138.3 | 0.0 | 33.4 | 100.0 | 33.4 | 0.0 | 0.0 | 0.0 | 4.9 |
| TMBTC | 0.0 | 0.0 | 0.0 | 0.0 | 0.0 | 0.0 | 14.3 | 0.0 | 2.0 | 0.0 |
| DMM | 0.0 | 0.0 | 0.0 | 0.0 | 0.0 | 0.0 | 10.2 | 0.0 | 0.0 | 0.0 |
| DMS | 0.0 | 0.0 | 0.0 | 0.0 | 0.0 | 0.0 | 26.7 | 0.0 | 0.0 | 0.0 |
| MeO-DMS | 0.0 | 0.0 | 0.0 | 0.0 | 0.0 | 0.0 | 16.2 | 0.0 | 0.0 | 0.0 |
| MeOH | 0.0 | 0.0 | 0.0 | 0.0 | 0.0 | 0.0 | 333.2 | 73.0 | 0.0 | 0.0 |
| NaOAc | 0.0 | 0.0 | 0.0 | 0.0 | 0.0 | 0.0 | 5.3 | 0.0 | 0.0 | 0.0 |
| Water | | 133.0 | 24.7 | 131.8 | | 131.8 | 72.6 | | | 25.7 |
| H$_2$SO$_4$ | | 38.2 | | 37.0 | | 37.0 | | | | 0.0 |
| H$_2$O$_2$ | | | | | | | | | | 0.0 |
| Graphite | | | | | | | | | | 0.0 |
| Maleic Acid | | | | | | | | | | 0.0 |
| Succinic Acid | | 1.2 | | 1.2 | 0.8 | | | | | 0.0 |
| Fumaric Acid | | | | | | | | | | 0.0 |
| 2-MeO-Succinic Acid | | | | | | | | | | 0.0 |
| TOTALS | 0.0 | 310.7 | 24.7 | 202.2 | 101.2 | 203.0 | 478.5 | 73.0 | 0.3 | 30.6 |

For the hydrolysis step of the process, a strong acid is definitely preferred, i.e. an acid which is highly dissociated in aqueous media. Mineral acids, such as sulfuric acid and phosphoric acid, and organosulfonic acid, such as benzenesulfonic acid and p-toluenesulfonic acid, can be used. Hydrochloric acid can also be used, but has the disadvantage of volatility, causing volatility losses, and of corrosiveness to equipment. Sulfuric acid works very well and will ordinarily be selected for use because of effectiveness, low cost and availability.

Example 18

Tests were conducted to determine the effect of temperature on the degree of recovery of tetramethyl butanetetracarboxylate from methanol, and the solubility of the compound in methanol at temperatures in the range of interest. The starting concentration was about 25% of the TMBTC compound. Results are reported in Table 10.

TABLE 10

| Temp. (°C.) | Recovery (%) | Solubility (%) |
|---|---|---|
| −11 | 87.8 | 5.07 |
| −7 | 83.5 | 6.49 |

TABLE 10-continued

| Temp. (°C.) | Recovery (%) | Solubility (%) |
|---|---|---|
| −6 | 82.2 | 7.32 |
| −1 | 78.6 | 9.22 |

Example 19

A methanol solution containing TMBTC and various impurities was separated by crystallization and filtration into 33% crystals and 67% filtrate, and partition of the various components between crystals and filtrate was determined at −10° C. temperature with results reported in Table 11.

TABLE 11

| | MeOH (%) | DMM (%) | DMS (%) | MeO-DMS (%) | TMBTC (%) |
|---|---|---|---|---|---|
| Crystals | 2.7 | 0 | 7.4 | 0 | 83.2 |
| Filtrate | 97.3 | 100 | 92.6 | 100 | 16.8 |

From the results in Table 10 it is evident that lower temperatures markedly improve TMBTC recovery, with −11° C., the lowest temperature shown, giving the best results. The results in Table 10 show that the crystallization is an effective means to separate TMBTC from various impurities, as well as from the methanol solvent.

Example 20

The effect of water on the recovery of TMBTC from methanol solution was tested, employing about a 25% TMBTC concentration and a $-10°$ C. crystallization temperature. Results are reported in Table 12.

TABLE 12

| % Water | % TMBTC Recovered |
|---|---|
| 0 | 88.1 |
| 5 | 89.9 |
| 10 | 90.6 |
| 20 | 92.9 |
| 40 | 94.1 |
| 75 | 97.6 |

The percentages of water are based on the total solution, i.e. 75% water mans a solution with 75% water content. It is evident that the recovery is improved by increasing the water content. Of course, additional water utilizes space in the crystallizer, thereby lessening the payload of TMBTC.

The use of water in the crystallization medium can improve the separation from dimethyl succinate, although this will vary considerably with the percentages of water employed. Table 13 shows the variance in TMBTC composition with % water content.

TABLE 13

| | COMPOSITION OF TMBTC | | | |
|---|---|---|---|---|
| Water (%) | TMBTC (%) | DMS (%) | CH$_3$OH (%) | Water (%) |
| 0 | 88.1 | 10.6 | 6.0 | 0.3 |
| 5 | 77.8 | 12.7 | 8.0 | 1.5 |
| 10 | 75.3 | 13.1 | 8.9 | 2.7 |
| 20 | 75.2 | 10.8 | 8.3 | 5.7 |
| 40 | 75.0 | 9.2 | 5.8 | 10.0 |
| 75 | 73.5 | 5.6 | 2.6 | 18.3 |

Filtrations of the TMBTC solution have been found very useful for their effect upon later extraction procedures, particularly when the solutions were obtained by EHD reactions. The filtrations are employed to filter out insoluble impurities from the TMBTC solutions. In a particular case, an unfiltered EHD solution took up about ⅓ of the volume of an extractor with a rag layer, which resisted separation. With a filtered EHD solution, the rag layer was only about 5% of mass.

The starting TMBTC solution utilized herein, as obtained by an EHD reaction of dimethyl maleate, is characterized by the presence of small amounts of particular reactants, by-products and other impurities. Among those materials included are dimethyl maleate, dimethyl succinate, and methoxydimethylsuccinate. These materials are separated fairly effectively in a crystallization and filtration step, as the materials largely remain in the methanol and go to filtrate, while the TMBTC is filtered out as crystals.

Water extractions, as used in the processing, are useful for removing electrolyte salt and some color materials. Some methanol is also removed, but this has little significance as methanol is produced and removed downstream in the hydrolysis stage. A TMBTC solution, as provided from an EHD reaction, has a yellow color. This can be from corrosion of connections, e.g. titanium connections, on EHD electrodes, and from organic color bodies. The water extractions mostly remove the color from the titanium, and partially remove that from organic contaminants. A second extraction appears to remove color beyond that removed by the first extraction. However, the number of extractions to be used will depend upon the degree of contamination, as well as the time and efficiency of the extraction procedure. Also the extractions can be tailored to that which is appropriate in conjunction with a later oxidation treatment to have a sufficient removal of color or color-forming materials. The extractions also remove salts, e.g. sodium acetate. The water extractions can very suitably be performed with the tetramethyl butanetetracarboxylate being the material purified, as this ester has very limited water solubility. In contrast, the downstream hydrolysis product, butanetetracarboxylic acid, has a fair degree of water solubility and would not lend itself to efficient extraction. The term "extraction" is used herein in the sense that the TMBTC is washed with water to extract impurities therefrom, while the TMBTC itself is not dissolved in the aqueous system. For the extractions, any effective way of mixing the TMBTC with an aqueous system, following by separation can be used. Rather than the batch system illustrated herein, a counter-current system could be employed in which streams are mixed and then separated.

There are various possible approaches and routes to preparation of butanetetracarboxylic acid which do not involve tetraalkyl butanetetracarboxylates From theoretical considerations, tetraalkyl butanetetracarboxylates might be expected to be difficult to hydrolyze, as involving four electron-withdrawing groups on adjacent carbon atoms. However, using procedures in accordance with the present invention it has been found feasible to hydrolyze tetraalkyl butanetetracarboxylates to virtually 100% completion, hydrolyzing all four ester groups, in reasonable reaction times and with nearly quantitative yields; and to conduct an overall process with various purification procedures, starting with a tetraalkyl butanetetracarboxylate still in its preparative reaction mixture, as e.g. an EHD electrolysis solution, and obtain butanetetracarboxylic acid of acceptable purity in overall yield of 80-85%.

What is claimed is:

1. A process for producing 1,2,3,4-butanetetracarboxylic acid which comprises subjecting a liquid electrolysis medium containing dialkyl maleate, an alkanol, and an alkanol-soluble alkali metal carboxylate supporting electrolyte to electrolysis, using a graphite anode and a graphite cathode, to obtain a tetraalkyl butanetetracarboxylate, and hydrolyzing the tetraalkyl 1,2,3,4-butanetetracarboxylate to obtain the 1,2,3,4-butanetetracaroxylic acid.

2. The process of claim 1 in which the dailkyl maleate is dimethyl maleate and the alkanol is methanol.

3. The process of claim 2 in which tetramethyl butantetracarboxylate is separated from the electrolysis medium with cooling and cyrstallization and subsequently hydrolyzed.

4. The process of claim 2 in which the initial concentration of dimethyl maleate is at least 15% by weight and the electrolysis is continued until at least about 95% of the dimethyl maleate has reacted.

5. The process of claim 2 in which hydrolysis is effected with a mineral acid catalyst to a temperature sufficient to distill methanol.

6. The process of claim 5 in which tetramethyl butanetetracarboxylate is hydrolyzed by heating an aqueous mixture containing at least 25% by weight thereof and a mineral acid in an amount sufficient to provide a gram equivalents acid/kg of reaction mixture of at least 1/1 to distillation temperature and distilling methanol as reaction proceeds and adding water to replace water removed by distillation, and substantially completing the hydrolysis within about six hours.

7. The process of claim 5 in which residual acid is neutralized by treatment with base.

8. The process of claim 2 in which the butanetetracarboxylic acid is treated with an oxidizing agent to remove color-causing materials.

9. The process of claim 8 in which the oxidizing agent is hydrogen peroxide.

10. The process of claim 8 in which an aqueous mixture of the butanetetracarboxylic acid is heated with hydrogen peroxide to temperatures up to about 55° C. to remove color-causing materials and then to higher temperature to decompose excess peroxide.

11. The process of claim 1 in which the alkanol-soluble alkali metal carboxylate supporting electrolyte is sodium acetate.

12. The process of claim 1 in which tetraalkyl butanetetracarboxylate is separated from the electrolysis medium by crystallization and filtration, extracted with water to remove water-soluble impurities, hydrolyzed by heating with water and acid to temperatures sufficient to distill alkanol, and treated with an oxidizing agent to remove color-causing materials.

13. The process of claim 12 in which the maleate is dimethyl maleate, the alkanol is methanol, and tetramethyl butanetetracarboxylate is produced and hydrolyzed.

* * * * *